United States Patent [19]

Montgomery

[11] Patent Number: 6,083,922
[45] Date of Patent: *Jul. 4, 2000

[54] METHOD AND A TOBRAMYCIN AEROSOL FORMULATION FOR TREATMENT PREVENTION AND CONTAINMENT OF TUBERCULOSIS

[75] Inventor: Alan Bruce Montgomery, Bellevue, Wash.

[73] Assignee: Pathogenesis, Corp., Seattle, Wash.

[ * ] Notice: This patent issued on a continued prosecution application filed under 37 CFR 1.53(d), and is subject to the twenty year patent term provisions of 35 U.S.C. 154(a)(2).
This patent is subject to a terminal disclaimer.

[21] Appl. No.: 08/825,725

[22] Filed: Apr. 2, 1997

Related U.S. Application Data

[60] Provisional application No. 60/014,630, Apr. 2, 1996.

[51] Int. Cl.[7] .................................................. A61K 31/70
[52] U.S. Cl. ............................... 514/38; 514/924; 424/43
[58] Field of Search ....................... 514/38, 924; 424/43

[56] References Cited

U.S. PATENT DOCUMENTS

| | | | |
|---|---|---|---|
| 4,761,402 | 8/1988 | Williams et al. | 514/54 |
| 5,006,343 | 4/1991 | Benson et al. | 424/450 |
| 5,284,133 | 2/1994 | Burns et al. | 128/200.23 |
| 5,508,269 | 4/1996 | Smith et al. | 574/38 |

OTHER PUBLICATIONS

Arnold L. Smith, M.D., et al., Safety of Aerosol Tobramycin Administration for 3 Months to Patients With Cystic Fibrosis, *Pediatric Pulmonolgy*, 7:265–271 (1989).

*Primary Examiner*—Elli Peselev
*Attorney, Agent, or Firm*—Hana Verny

[57] ABSTRACT

A method for treatment, prevention and containment of acute and chronic tuberculosis using a preservative-free concentrated tobramycin aerosol formulation delivering tobramycin to the lung endobronchial space including alveoli in an aerosol having mass medium average diameter predominantly between 1 to 5$\mu$. The method comprises administration of tobramycin in concentration one to ten thousand times higher than the minimal inhibitory concentration of *Mycobacterium tuberculosis*. A method for containment of and decreasing infectivity periods of tuberculosis patients to shorter periods of time.

20 Claims, 4 Drawing Sheets

METHOD AND A TOBRAMYCIN AEROSOL FORMULATION FOR TREATMENT PREVENTION AND CONTAINMENT OF TUBERCULOSIS

This application is based on a provisional application Ser. No. 60/014,630 filed on Apr. 2, 1996.

BACKGROUND OF THE INVENTION

FIELD OF INVENTION

The current invention concerns a method for treatment, prevention and containment of tuberculosis using a tobramycin aerosol formulation. In particular, the invention concerns a preservative-free formulation containing concentrated tobramycin dissolved in full strength or diluted saline adjusted to pH between 5.5 and 7.0. The tobramycin aerosol formulation delivers tobramycin to the lung endobronchial space of airways including alveoli in an aerosol having mass medium average diameter predominantly between 1 to 5μ. The method for treatment and prophylaxis of acute and chronic tuberculosis caused by the *Mycobacterium tuberculosis* comprises administration of tobramycin in concentration one to ten thousand times higher than the minimal inhibitory concentration of *Mycobacterium tuberculosis*. The invention additionally provides a method for containment of infectivity of tuberculosis patients to shorter periods of time.

BACKGROUND ART AND RELATED ART DISCLOSURES

*Mycobacterium tuberculosis* or *Tuberculum bacilli* (T. B.) grows in the endobronchial space and is found in the sputum of infected individuals. During exacerbations of infection, such growth also occurs in the alveoli.

Tuberculosis is a highly infectious disease that is characterized by the inflammation and progressive destruction of lung tissue. The debilitation of the lungs in patients with tuberculosis is associated with accumulation of purulent sputum produced as a result of chronic endobronchial infections caused by *Mycobacterium tuberculosis*. Nearly all individuals suffering from tuberculosis eventually die of respiratory failure.

Presently, administration of drugs, such as aminoglycosides kanamycin, streptomycin and amicacin as well as isoniazid is the treatment of choice for tuberculosis patients. However, penetration of these drugs into the bronchial secretions is poor at approximately only about 12% of the peak serum concentration (*Rev. Infect. Dis.*, 3:67 (1981)). According to *Advances in Pediatric Infections Diseases*, 8:53 (1993), sputum itself is inhibitory to the bioactivity of aminoglycosides because of its high ionic strength and the presence of divalent cations. Sputum also contains mucin glycoproteins and DNA, which bind aminoglycosides making them less effective.

The inhibitory activity of glycoproteins may be overcome by increasing the concentration of aminoglycosides in the sputum to ten times the minimum inhibitory concentration of the particular isolate (*J. Infect. Dis.*, 148:1069 (1983)). This presents a serious problem because aminoglycosides are poorly transported into sputum. Therefore, to achieve therapeutic concentrations in sputum, high doses of the drug delivered parenterally are required. The high doses of the parenterally administered drugs increase the risk of systemic toxicity including ototoxicity and nephrotoxicity. Parenteral therapy also increases patient hardship because it requires hospitalization, exposes the patient to other potential infections and generally increases treatment costs.

Attempts were made recently to administer aminoglycosides by aerosol. For example, effective aerosol administration of aminoglycosides for treatment of cystic fibrosis pulmonary infections is described in the U.S. Pat. No. 5,508,269. The formulation described therein enabled delivery of aminoglycosides in aerosolized particles having sizes between 1–5μ. The method described in the '269 patent overcomes prior disadvantages of many nebulizers which produce an aerosol comprising a large number of aerosol particles in the range of 50–100μ.

In order to be therapeutically effective, the majority of aerosolized drug particles should not have larger mass medium average diameter (MMAD) than between 1 and 5μ. When the aerosol contains a large number of particles with a MMAD larger than 5μ, these are deposited in the upper airways decreasing the amount of the drug delivered to the site of infection in the lower respiratory tract.

In view of the above described disadvantages of systemic treatment of tuberculosis, it would be highly advantageous to provide a method for treatment and prevention of *Mycobacterium tuberculosis* infections by a locally administered anti-tuberculosis drug in an aerosol form.

It is, therefore, a primary objective of this invention to provide a method and a regimen for treatment, prevention and containment of infectivity of tuberculosis by a concentrated aerosol formulation containing a sufficient amount of an anti-*Mycobacterium tuberculosis* drug to eradicate or substantially suppress *Mycobacterium tuberculosis* bacterium.

SUMMARY

One aspect of the current invention is a method for treatment, prevention and containment of pulmonary tuberculosis or other infections caused by *Mycobacterium tuberculosis, Mycobacterium bovis* or other mycobacteria by administering to a subject requiring such treatment a formulation comprising about a one to ten thousands times higher concentration of tobramycin than is its minimal inhibitory concentration.

Another aspect of the current invention is a method for treatment, prevention and containment of pulmonary tuberculosis caused by *Mycobacterium tuberculosis*, by administering to a subject requiring such treatment twice daily, for at least five days, a formulation comprising about 8 to about 80 mg/mL of tobramycin dissolved in a full or quarter normal saline having a pH between 5.5 and 7.0 and delivered by a jet or ultrasonic nebulizer in 5 mL concentrated form in an aerosol producing a particle size having the mass medium average diameter predominantly between 1 and 5μ.

Still another aspect of the current invention is a method for treatment of pulmonary infections caused by *Mycobacterium tuberculosis* by administering to a subject requiring such treatment a formulation comprising about 300 mg of tobramycin dissolved in 5 mL of a quarter normal saline adjusted to a pH about 5.5 to about 6.5.

Still yet another aspect of the current invention is an aerosol formulation comprising concentration from about 8 to about 80 mg/mL of tobramycin dissolved in about 5 mL of a full or quarter normal strength saline wherein said tobramycin concentration is one to ten thousand times higher than the minimal inhibitory concentration of tobramycin.

DEFINITIONS

As used herein:

"MIC" means minimal inhibitory concentration able to reduce the count of M. tuberculosis in sputum to less than $10^3$.

"M. tuberculosis", "MTB", or "T.B." means bacterium Mycobacterium tuberculosis or tuberculum bacilli.

"T.B. infected" or "tuberculosis infected" patients means patients having a detectable count of M. tuberculosis bacterium in sputum smear higher then $10^3$.

"CFU" means colony forming units.

"Normal saline" means water solution containing 0.9% sodium chloride (NaCl).

"Diluted saline" means normal saline containing 0.9% NaCl diluted into its lesser strength.

"Quarter normal saline" or "¼ NS" means normal saline diluted to its quarter strength containing 0.225% NaCl.

DETAILED DESCRIPTION OF THE INVENTION

Figure 1:
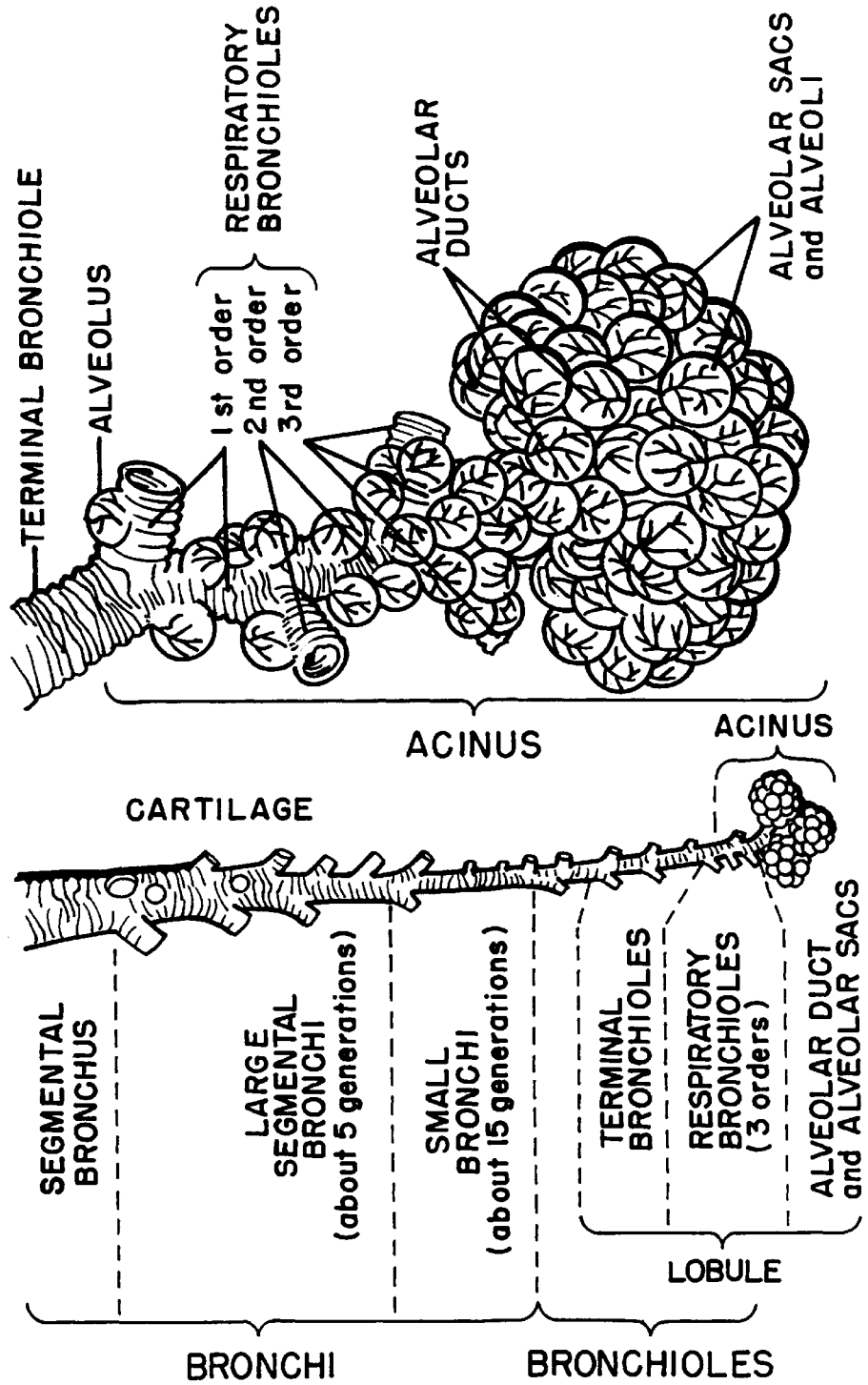
FIG. 1 depicts subdivisions and structure of intrapulmonary airways.

The current invention is based on finding that tobramycin in concentrations between 8 and 16 µg/mL is able to substantially and continuously reduce a count of Mycobacterium tuberculosis responsible for highly infectious pulmonary tuberculosis. In the killing curve assay following the treatment with tobramycin, the count of Mycobacterium tuberculosis expressed in colony forming units (CFU), decreased from $10^6$ to about $10^2$.

The current invention, therefore, concerns a method for prevention and treatment of pulmonary tuberculosis and for containment and reduction of an infected individual's infectivity. The invention also concerns a concentrated tobramycin formulation suitable for efficacious delivery of tobramycin by aerosolization into endobronchial space. The method of the invention is most preferably suitable for prevention of development of pulmonary tuberculosis in individuals subjected to contact with a tuberculosis infected subject, for treatment of the subject already infected with tuberculosis as well as for containment and decreasing the infectivity time of the infected individuals.

The method involves providing to the individual in need of any of the above mentioned treatment an aerosolized tobramycin in concentration sufficient to decrease the count of Mycobacterium tuberculosis to levels lower than $10^3$ and to contain and decrease the infectivity of tuberculous patients to several days rather than weeks or months.

High concentrations of tobramycin administered to the lungs by aerosolization result in maximization of sputum levels of tobramycin and in minimization of tobramycin serum levels. Thus, administration of tobramycin by aerosolization has the advantage of reducing systemic toxicity while providing efficacious concentrations of tobramycin in the sputum. The bronchial barrier restricts the movement of aerosolized tobramycin and prevents it from reaching high systemic levels.

Aerosolized formulation of tobramycin delivers high concentrations of the drug directly to the airways with low systemic absorption. Aerosolized formulation of concentrated tobramycin is nebulized by jet or ultrasonic nebulizers able to produce tobramycin aerosol having particle size predominantly between 1 and 5µ. Particles of these sizes are necessary for efficacious delivery of concentrated tobramycin into endobronchial space in order to treat pulmonary tuberculosis infections. To achieve high concentrations of tobramycin solution in both the upper and lower airways and in sputum, tobramycin is preferably nebulized in jet nebulizers, particularly those modified with the addition of one-way flow valves, such as, for example, Pari LC Plush nebulizer, commercially available from Pari Respiratory Equipment, Richmond, Va., which delivers up to 20% more drug than the other unmodified nebulizers.

The tobramycin aerosol formulation contains a high concentration from about 8 to about 80 mg/mL, preferably about 60 mg/mL of tobramycin sufficient for M. tuberculosis suppression or eradication, formulated in the smallest possible volume of about 1–5 mL of a physiologically acceptable solution, preferably in one quarter strength of normal saline, having a salinity adjusted to permit generation of tobramycin aerosol well-tolerated by patients but to prevent the development of secondary undesirable side effects such as bronchospasm and cough.

The invention therefore provides a primary means for prophylaxis or treatment of pulmonary tuberculosis as well as a means for substantial containment and decreasing infectivity time of subjects infected with tuberculosis. The invention also provides means for an adjunct therapy for general M. tuberculosis infections.

One aspect of the invention is a therapy of the highly infectious pulmonary tuberculosis which devastates the patient and without treatment is often fatal. While some effective drugs are available and efficacious in treatment of tuberculosis, they often lead to the development of the M. tuberculosis bacterium resistance and with time become either much less or completely ineffective. Moreover, as described above, the systemic treatment of tuberculosis leads to development of various undesirable side effects.

The new aerosol therapy of the invention enables localized delivery of the effective anti-tuberculosis drug tobramycin to a site where the bacterium resides and in this way enables the suppression and eradication of the tuberculosis.

In another aspect, the invention is useful for prophylactic purposes. Due to its high infectivity, tuberculosis is highly contagious even under most normal circumstances, that is by being subjected to a contact with the infected individual. Since the infection is spread by small droplets generated by coughing of the infected individual, there is no practical way of avoiding it. The method for prophylaxis, according to the invention, treat the individual being in contact or being previously subjected to the contact with a tuberculosis patient with sufficiently high concentration of tobramycin able to prevent growth of M. tuberculosis bacterium.

One other important aspect of the invention is the method for containment and decreasing infectivity of tuberculosis patients.

Tuberculosis is a very infectious disease, spread and transmitted by coughing which creates small aerosol droplets containing Mycobacterium tuberculosis bacteria. These bacteria come from any part of the airways in upper lung or in lower lung or alveoli of the lung. In addition, the larynx of tuberculosis patients is highly infectious and the patients, therefore, need to be hospitalized in an isolation room until the treatment suppresses the *M. tuberculosis* in sputum. Currently, this may take one to two months or longer depending on the *Mycobacterium tuberculosis* strain resistance. To deliver systemically doses high enough to suppress the *M. tuberculosis* in sputum typically requires high dosages of drugs, takes a long time and it often leads to severe undesirable secondary symptoms.

These obstacles are overcome by the method of the invention which provides high concentration of tobramycin delivered locally directly to the upper lung, lower lung, alveoli and sputum as well as to the larynx. High concentrations of aerosolized tobramycin delivered directly to the lung and to the sputum inhibits the bacterium growth and kills the bacteria and decreases infectivity of the tuberculosis patient in a very short time of several days rather than months.

Lowest systemic minimal inhibitory concentration of tobramycin is around 8 $\mu$g/mL. Maximum safe concentration of tobramycin in the serum is between 8–10 $\mu$g/mL. Such concentration of systemically administered tobramycin has little or no effect on *M. tuberculosis* present in the lung and particularly in the sputum as it cannot penetrate the sputum and/or achieve sufficiently high concentration to kill the bacteria. For these reasons, tobramycin is currently considered an unsuitable drug for treatment of tuberculosis. On the other hand, as the minimum inhibitory concentration needed for suppression or eradication of T.B. is 8 $\mu$g, such amount of tobramycin if delivered locally and directly to the sputum in an aerosolized form would suppress and eradicate the bacteria in the sputum. However, until now such direct delivery of tobramycin into lungs in amounts sufficient to penetrate the sputum and kill the bacteria was not available.

The tobramycin aerosol formulation of the invention contains at least one thousand but usually about ten thousand times higher concentration of tobramycin than is its minimum inhibitory amount. Tobramycin is nebulized predominantly into particle sizes which are delivered to the terminal and respiratory bronchioles and alveoli (lower lungs) where the *M. tuberculosis* is present in patients infected with tuberculosis as well as in the upper lung and larynx where *M. tuberculosis* is also present and which is responsible for patient's infectivity. Moreover, high concentration of aerosolized tobramycin comes into contact with the sputum, penetrates it and kills bacteria present there.

Subdivision and structure of intrapulmonary airways (lower lung) are seen in FIG. 1. *M. tuberculosis* is present in the upper airways, in bronchi and bronchioli, particularly in terminal and respiratory bronchioles. During exacerbation of infection, bacteria can also be found to be present in alveoli. Any therapeutic formulation must be, therefore, delivered to the terminal bronchioles and to alveoli.

I. Method for Treatment and Prophylaxis of Tuberculosis

The current invention provides a safe and efficacious method for treatment and prophylaxis of pulmonary *Mycobacterium tuberculosis* infections.

Primary requirements for any method of treatment and prophylaxis as well as for any aerosolized formulation are its safety and therapeutic and prophylactic efficacy. Lower cost, practicality of use, long shelf-life of the formulation, its storage and manipulation of the nebulizer are also definite consideration for any treatment. The current method and the aerosol formulation used in the method provides all the above advantages.

Briefly, the method for treatment for prophylaxis comprises administering to a patient diagnosed with a pulmonary tuberculosis or a subject being in contact with the patient having *Mycobacterium tuberculosis* present in the sputum, about 40 to about 800, preferably about 300 mg of nebulized tobramycin once or twice daily for at least five or more consecutive days, depending on the treatment.

For the method of treatment, patients are first screened for pulmonary tuberculosis bacilli by the presence of acid-fast bacilli in expectorated sputum. If such presence is detected, the patients are treated according to the method of the invention. Quantitative determination of *Mycobacterium tuberculosis* in the sputum is performed before, during and after administration of tobramycin twice daily. The treatment of tuberculosis continues until the *Mycobacterium tuberculosis* count in the sputum is lower than $10^3$ or undetectable.

For the prophylaxis, a subject which is or was subjected to contact with a tuberculosis patient is treated with tobramycin formulation comprising about 80 to about 300 mg of tobramycin once or twice daily and the presence or absence of *Mycobacterium tuberculosis* in sputum is followed.

The *Mycobacterium tuberculosis* count or the absence thereof in the lung is determined before the prophylactic treatment is initiated. If the patient has no detectable count of *Mycobacterium tuberculosis* in the sputum or in the smear from the larynx, the formulation containing lower concentrations of tobramycin, preferably from about 100 to about 200 mg is administered preventatively once or twice daily for at least five days.

If the subject has detectable *Mycobacterium tuberculosis* in the sputum or in the larynx but did not yet develop typical symptoms accompanying the tuberculosis infection, then the patient is given prophylactic doses of the aerosolized tobramycin comprising about 200 to about 300 mg of tobramycin twice daily for five days. This prophylactic treatment is sufficient to eliminate the bacterium and/or prevent its growth.

Additionally, the method of the invention is useful for suppressing infectivity and spread of tuberculosis by already infected individuals. Active pulmonary tuberculosis is per se highly infectious disease and is easily transmitted by coughing which creates small aerosol droplets containing T.B. bacteria. These bacteria can come from any part of the airways or alveoli of the lung. Most often, however, they are from the highly infectious larynx. The method for suppressing infectivity utilizes locally administered high concentrations of tobramycin to decrease both the infectivity as well as the period of time during which the patient is infective even after initiation of therapy. The method essentially utilizes local administration, by aerosol, by spray or by smearing of the patient's mouth and throat with the solution of concentrated tobramycin comprising between 100 and 600 mg of tobramycin as many times daily as necessary.

Figure 2:
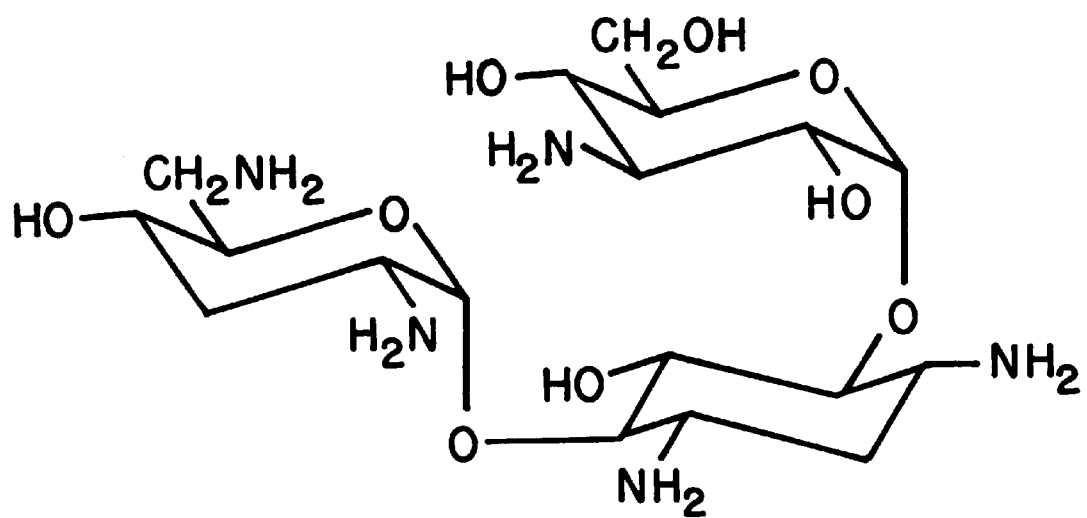
FIG. 2 illustrates a structure of tobramycin.

Tobramycin is an antibiotic having a chemical structure seen in FIG. 2. Tobramycin has now been found to possess anti-*Mycobacterium tuberculosis* bactericidal activity responsible for an observable decrease in quantitative spectrum counts of *Mycobacterium tuberculosis* during the first two days of therapy according to the invention. The early bactericidal activity of tobramycin is its inherent property which is comparable to tobramycin activity measured in vitro, in logarithmic plot cultures. Results of the in vitro study performed according to *Am. Rev. Respir. Dis.*, 21:939 (1980) are seen in FIG. 4.

Figure 4:
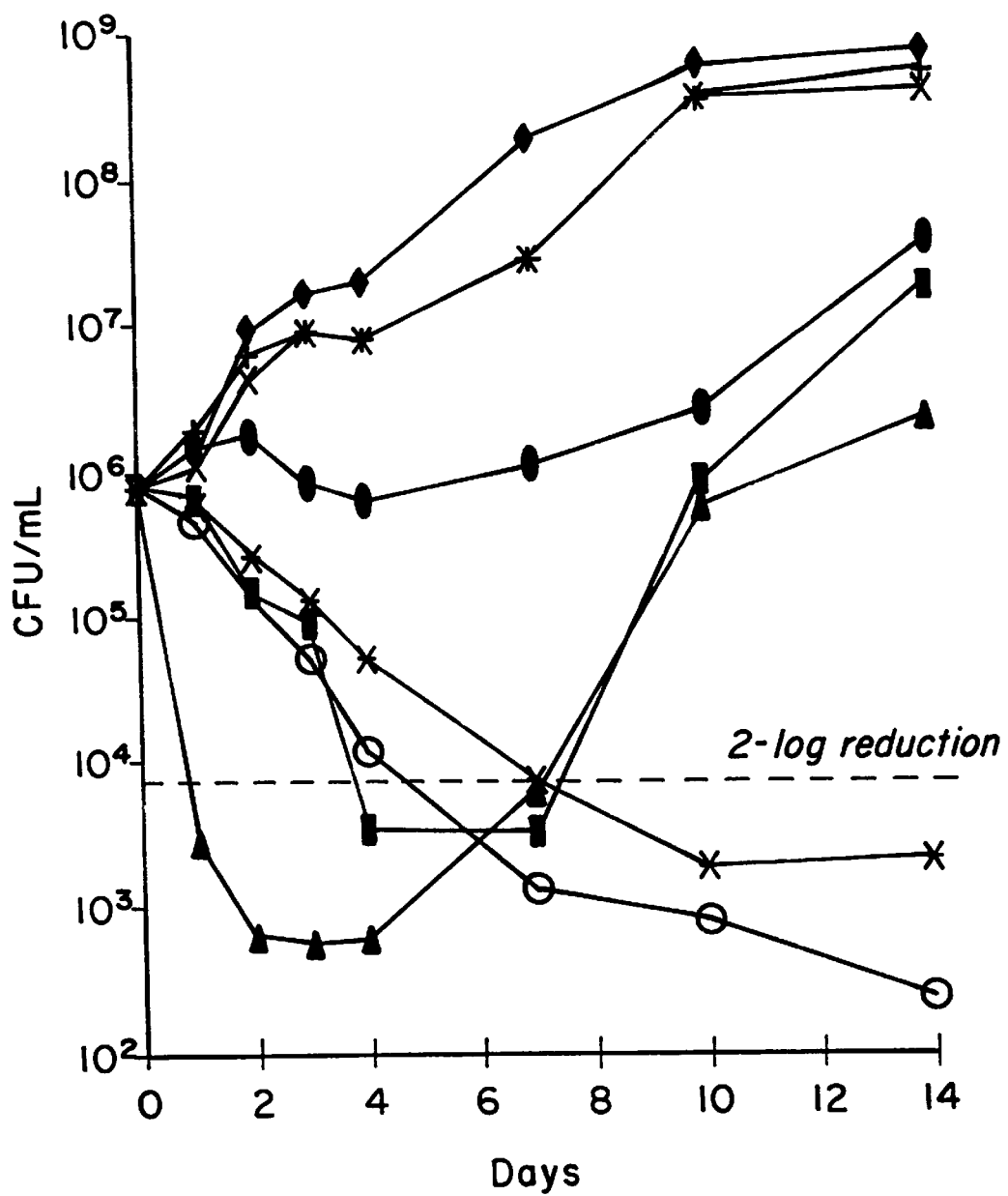
FIG. 4 is a graph depicting results of killing curve assay for tobramycin compared to isoniazid.

FIG. 4 is a graph showing results of a Killing Curve assay for tobramycin. Tested tuberculosis strain, *M. tuberculosis* H37Rv(lux), contains a luciferase reporter construct, and has similar growth characteristics to *M. tuberculosis* H37Rv. For this study, cultures containing $10^6$ CFU/mL of *M. tuberculosis* H37Rv (lux), grown in Middlebrook 7H9 medium were incubated with various concentrations of antibiotic tobramycin or a known anti-tuberculosis drug isoniazid (INH). Bactericidal activity of these two drugs, at the indicated concentrations, were compared to cultures grown without antibiotics, serving as a growth control. Aliquots were withdrawn at the indicated timepoints for quantitation by serial dilution.

As seen in FIG. 4, tobramycin shows potent activity against M. tuberculosis H37Rv in vitro. Even very low concentrations of tobramycin (1–2 μg/mL) assert bactericidal activity decreasing the count of *M. tuberculosis* when compared to the growth control. At 4 μg/mL, tobramycin is able to prevent growth of *M. tuberculosis* for about eight days and only after that time, the bacteria again start to grow. At 8 and 16 μg/mL concentration, tobramycin has a substantial bactericidal activity leading to more than 2-log reduction of *M. tuberculosis* counts in vitro. When 8 μg/mL concentration of tobramycin is used, growth of the bacteria, expressed as CFU/mL and expressed in the log reduction, is seen to be inhibited at day 7. At 16 μg/mL tobramycin concentration, 2-log reduction is reached at day four. Moreover, both these concentrations are sufficient to achieve the initial reduction in the count and killing of bacteria but also to maintain this effect. These results were contrary to results obtained with isoniazid. Administration of isoniazid results in initial sharp killing of bacteria observable at day 1 at concentration of 0.25 μg/mL of isoniazid and at day 4 at concentration of 0.06 μg/mL of isoniazid. However, as seen in FIG. 4, neither of these effects lasted, and in both cases, the growth of the bacteria resumed at day 4 for 0.06 μg/mL, and at day 7 for 0.25 μg/mL of isoniazid. Isoniazid bactericidal activity was, therefore, only temporary. The treatment with tobramycin, on the other hand, resulted in continuous decrease and inhibition of *M. tuberculosis* growth.

Achieving inhibitory and preferably bactericidal concentrations of the active drug in bronchial secretions is important in pneumonic processes, insofar as pneumonia is a mixture of parenchymal infection and tracheobronchitis. An intravenously-administered drug typically does not reach necrotic infected tissue in tubercular cavities, where large numbers of *M. tuberculosis* bacilli reside. By providing high concentrations of drug in the alveolar and bronchial space, rapid killing of the extracellular population of bacilli is assured. Tobramycin delivered by the aerosol route achieves significant concentrations in lung parenchyma. An aerosol drug delivered directly to the bronchial and alveolar space is therefore a useful addition to current antituberculosis drug regimens.

*Mycobacterium tuberculosis* encompasses a variety of multidrug-resistant strains which are more or less resistant to treatments with various drugs such as isoniazide, streptomycin, kanamycin, rifampin and ethanbutol. Many of these strain were shown to be sensitive and nonresistant to treatment with tobramycin.

Results of the comparative resistance study are seen in Table 1. In Table 1, drug resistance was determined by BACTEC test commercially available from Becton-Dickinson. BACTEC test which measures growth of bacteria by detecting the utilization of $C^{14}$ labeled substrate, was performed with the following drug concentrations (μg/mL): isoniazid 0.4 μg/mL; rifampin 2 μg/mL; streptomycin 6.0 μg/mL; kanamycin 5.0 μg/mL and ethanbutol (EMB) 7.5 μg/mL. Tobramycin concentrations needed to achieve minimal inhibitory concentration (MIC; μg/mL) are seen in Table 1.

TABLE 1

Activity of Tobramycin Against Drug-Sensitive Strains of *M. tuberculosis*

| Drug Sensitive Strain | Tobramycin MIC (μg/mL) |
|---|---|
| H37RV | 4 |
| TN994 | 4 |
| TN2351 | 8 |
| TN3183 | 4 |
| TN675 | 4 |
| TN2524 | 4 |
| TN4259 | 4 |
| TN1008 | 4 |
| TN1039 | 4 |
| TN3979 | 4 |

TABLE 2

Activity of Tobramycin Against Multidrug-Resistant Strains of *M. tuberculosis*

| Multidrug Sensitive Strain | Resistance1 MIC (μug/mL) | Tobramycin |
|---|---|---|
| TN702 | INH, SM | 4 |
| TN715 | INH, RIF, SM | 4 |
| TN768 | INH, RIF, SM, EMB | 8 |
| TN1195 | INH, SM | 4 |
| TN1314 | INH, RIF | 8 |
| TN1811 | INH, RIF, SM, EMB | 4 |
| TN2557 | INH, RIF, SM | 8 |
| TN565 | INH, RIF, SM, KAN | >128 |
| TN576 | INH, RIF, SM, EMB, KAN | >128 |
| TN587 | INH, RIF, SM, EMB, KAN | >128 |
| TN2015 | INH, RIF, SM, KAN | >128 |
| TN3806 | INH, RIF, SM, EMB, KAN | >128 |

A survey of tobramycin MICs for drug-sensitive and multidrug-resistant strains of *M. tuberculosis* demonstrate that the majority of isolates have minimal inhibitory concentrations (MICs) ≦8 μg/mL. The tested strains which are highly resistant to tobramycin with MIC>128 μg/mL represent a minority of clinical isolates of *M. tuberculosis.*

As seen in Table 1, tobramycin had a bactericidal activity at very low, 4–8 μg/mL, minimal inhibitory concentration in all tested drug sensitive strains. Activity of tobramycin against multidrug-resistant strains which are resistant to two or more drugs currently used for treatment of tuberculosis, was between 4–8 μg/mL against more than half of the multidrug-resistant strains. These results show that tobramycin has a good bactericidal activity against most strains of *Mycobacterium tuberculosis*. Combined with the alternative way of delivery by locally administered aerosol, tobramycin may prove to be the safest yet and most efficacious available treatment of tuberculosis.

Locally administered tobramycin provides many advantages and assures the safety of the new treatment according to the invention. Minimal inhibitory concentration of systemically administered tobramycin is believed to be out of the safe range of tobramycin in serum. The maximum safe concentration range for tobramycin is between 8–10 μg/mL in the serum. However, to achieve the concentration which was found to be bactericidal, that is at least 8 μg/mL and above in the lungs and sputum, tobramycin would have to be present in the systemic circulation in a much higher concentration than the maximum safe concentration of 8–10 μg/mL. Absorption and transport of systemically administered tobramycin into lung parenchymal tissue is very low, in a ratio of probably less than 100:1 systemic/lung concentration. Consequently, the minimal inhibitory concentration which would need to be present in the systemic circulation would have to be at least 800–1000 µg/mL. Such concentrations are considered to be unsafe. For these reasons, tobramycin is generally not used for tuberculosis treatment.

While tobramycin concentrations of 8 µg/mL are difficult to achieve in sputum with parenteral administration, such and much higher concentrations may be achieved in the airways with minimal systemic toxicity using aerosol delivery.

Several studies have documented the safe delivery of high concentrations of tobramycin to the sputum using an aerosol route. Much of this work has been done toward treatment of chronic lung infections with *Pseudomonas aeruginosa* in cystic fibrosis (CF) patients and is described in U.S. Pat. No. 5,508,269, hereby incorporated by reference. A multicenter, double-blind, placebo-controlled cross-over trial in 71 CF patients of aerosolized tobramycin 600 mg three times daily (tid) for endobronchial infections due to *P. aeruginosa* demonstrated a significant reduction in sputum density of *P. aeruginosa* as well as improved spirometry in the treatment group.

A 600 mg tid regimen of aerosolized tobramycin was thus found to be both safe and efficacious in CF patients. Previous studies also indicated that sputum inhibits tobramycin activity, and that concentrations at least 5–10 times higher are needed to overcome this inhibition. Sputum tobramycin concentrations of at least 10–100 times the MIC therefore may be needed to provide therapeutic concentrations of tobramycin.

To achieve such concentrations, the drug must be formulated in an aerosol in a highly concentrated form and nebulized into the aerosol MMAD particles of sizes which will be able to reach and enter the upper as well as lower lung, including alveoles.

The tobramycin sputum concentrations provide useful estimates of drug delivery with aerosol administration. Observations on the binding of tobramycin by sputum indicated that sputum concentrations of 10–100 times MIC, or 80–800 µg/mL tobramycin, provide bactericidal activity toward *M. tuberculosis*. These concentrations and even those 100 or 200 times higher are achievable with the Pari LC Plus jet nebulizer.

The method for treatment according to the invention demonstrates the safety and efficacy of an aerosolized tobramycin regimen as monotherapy in the treatment of tuberculosis because the drug is active as a single agent on the extracellular population of *Mycobacterium tuberculosis* organisms.

As part of a multidrug regimen for tuberculosis, aerosolized tobramycin may be useful in several settings. Tobramycin activity against extracellular bacilli may be useful in reducing the time to culture conversion, reducing the infectivity of cases, and decreasing total treatment time. Aerosolized tobramycin according to the invention is a first-line antituberculosis drug in patients who have developed toxicity, allergic reaction or who have underlying conditions that preclude therapy with other existing first-line antituberculosis drugs. Aerosolized tobramycin may thus be effective in treating multidrug-resistant organisms which would otherwise remain untreatable.

II. Tobramycin Aerosol Formulation for Treatment and Prophylaxis of Tuberculosis Aerosolized tobramycin formulation of the invention is formulated for efficacious delivery of concentrated tobramycin to the lung endobronchial space for treatment and prophylaxis of tuberculosis. The formulation has adjusted salinity to permit generation of tobramycin aerosol well-tolerated by patients. Further, the formulation has balanced osmolarity ionic strength and chloride concentration. The formulation utilizes a smallest possible aerosolizable volume, preferably from about 3 to about 7 mL, most preferably 5 mL, able to deliver effective dose of tobramycin to the site of the infection. The tobramycin aerosolized formulation does not impair negatively the functionality of the airways and does not cause undesirable side effects.

The tobramycin formulation to be used for treatment or prophylaxis of tuberculosis according to the invention, contains from 40–800, preferably 100–400, and most preferably 300 mg of tobramycin sulfate per 5 mL of the quarter normal saline. This corresponds to 8–160, preferably 20–80 and most preferably 60 mg/mL of tobramycin, which represents less than about $10^4$ times minimal inhibition concentration of tobramycin. This formulation, delivered in nebulized form, suppresses the tuberculosis infection in endobronchial space rapidly within the several hours to several days.

Typically, the selected amount of tobramycin, as described above, is dissolved in 5 mL solution of saline, preferably a diluted, typically quarter normal saline, containing about 0.225% NaCl. The quarter normal saline has been found to be a most suitable vehicle for delivery of tobramycin into endobronchial space.

The effective dose of tobramycin will depend on its intended use. Tobramycin is optimally used in 40–100, preferably 60 mg/mL dosage for treatment of tuberculosis in adult subject. However, higher or lower dosages are also conveniently delivered by the aerosol formulation and will depend on whether used in children or adults, or whether used for therapy, prevention or containment of *M. tuberculosis*.

Aerosol formulation of the invention is conveniently nebulized in suitable jet or ultrasonic nebulizers provided certain conditions are met. Jet and ultrasonic nebulizers are both sensitive to the osmolarity of the formulation and ultrasonic nebulizers are additionally sensitive to the pH of the formulation and to its ionic strength. Therefore, it is preferred to formulate tobramycin in quarter normal saline, rather than in full strength 0.9% saline.

Such formulation is also preferable from the patient point of view. Patients with acute or chronic tuberculosis have substantially impaired lung function and high incidence of bronchospastic or asthmatic reactions. Their airways are sensitive to hypotonic or hypertonic aerosols, to the presence of a permanent ion, such as chloride, as well as to aerosols that are acidic or basic. Irritation of the airways is clinically manifested by coughing or bronchospasm. Both these conditions are not only irritating to the patient but also prevent efficient delivery of aerosolized tobramycin into the endobronchial space.

The tobramycin formulation containing about 60 mg of tobramycin per mL of ¼ NS has an osmolarity in the range of 165–190 mOsm/l. This osmolarity is within the safe range of aerosols administered to tuberculosis patients and is also suitable for nebulization.

Equally important for aerosol delivery is the pH of the formulation. When the aerosol is acidic or basic, it can cause bronchospasm and cough. The safe range of pH is relative and depends on a patient's tolerance. Some patients tolerate a mildly acidic aerosol which in others will cause bronchospasm. Typically, an aerosol solution having a pH less than 4.5 induces bronchospasm. The aerosol solution having pH between 4.5 and 5.5 will occasionally cause this problem. The aerosol solution having a pH between 5.5 and 7.0 is considered safe. Any aerosol having pH greater than 7.0 is to be avoided as the body tissues are unable to buffer alkaline aerosols and result in irritation and bronchospasm. For the safety of the patient, it is preferred that pH of the formulation is between 5.5 and 7.0, most preferably between 5.5 and 6.5.

The pH is also important for stability of the formulation. At pH greater than 7.0 degradation of tobramycin occurs. To determine the stability of the tobramycin formulation vis-a-vis its pH, four studies, described in Examples 3 and 4 were performed.

In the first stability study, described in Example 3, accelerated stability testing of 60 mg/mL tobramycin, at 40° C. temperature and at pH 7.0, showed after 35 days, yellowing of the solution indicating the presence of chromophore degradation product. Results are seen in Table 5. This finding was unexpected and not predicted by the literature on aminoglycoside degradation (*Drug Develop. Industr. Pharm.*, 18:1423–36 (1992)).

The above observed reaction was less apparent when the same testing was done at pH 5.5 or 6.5 (Table 5). At such pH, the degradation was either not present or was much slower. The optimal pH for the aerosol formulation was, therefore, determined to be between pH 5.5 to pH 6.5.

In two extended stability studies described in Example 4, the formulation was stable for more than 6 months at temperature 5° C. at about pH 6. Results are seen in Tables 6 and 7. Less stable was the formulation stored for 6 months at 25° C., where the color formation increased from 15 KS units to 52 KS units. Results are seen in Tables 8 and 9.

The formulation of the invention is nebulized predominantly into particle sizes allowing a delivery of the drug into both upper and lower lung including the terminal and respiratory bronchioles where the *Mycobacterium tuberculosis* resides, as seen in FIG. 1. For efficacious delivery of tobramycin to the lung endobronchial space of airways and particularly to alveoli in an aerosol, the formation of aerosol particles having mass medium average diameter (MMAD) predominantly between 1 to 5μ is necessary.

The formulated and delivered amount of tobramycin for treatment and prophylaxis of tuberculosis must effectively target the sputum produced by the bacterium. The formulation must have a smallest possible aerosolizable volume able to deliver effective dose of tobramycin to the site of the infection. The formulation must additionally provide conditions which would not adversely affect the functionality of the airways. Consequently, the formulation must contain enough of the drug formulated under the conditions which allow its efficacious delivery while avoiding undesirable reaction. The formulation according to the invention meets all these requirements and is, therefore, particularly suitable for treatment and prophylaxis tuberculosis according to the invention.

III. Nebulizers

The method of the invention depends on the efficacious delivery of tobramycin into the upper and lower lung, alveoli and sputum. For the efficacious delivery, the size of the aerosolized particles was found to be critical. Particles larger than 1–5μ were found to impact the upper airways in that these particles were largely deposited above the endobronchial space, in the oropharynx and in the mouth. As a result, the drug delivery to the lower lung was impaired, the patient's treatment and or prophylaxis was slowed or greatly impaired and a large amount of the drug was wasted.

A formation of the tobramycin aerosol particles having mass medium average diameter (MMAD) predominantly between 1 to 5μ depends on the nebulizer and the choice of the nebulizer is therefore critical for efficacious treatment according to the invention.

The nebulizer must be able to nebulize the formulation of the invention into aerosol particle size predominantly in the range from 1–5μ. Predominantly in this application means that at least 70%, but preferably more than 90%, of all generated aerosol particles are within 1–5μ range.

Two types of nebulizers, jet and ultrasonic, can produce and deliver particles between the 1 and 5μ particle size. A jet nebulizer works by air pressure to break a liquid solution into aerosol droplets. An ultrasonic nebulizer works by a piezoelectric crystal that shears a liquid into small aerosol droplets.

While the range variety of nebulizers is available, only limited number of these nebulizers are suitable for the purposes of this invention. One representative nebulizer suitable for purposes of this invention is illustrated in FIG. 3.

Figure 3:
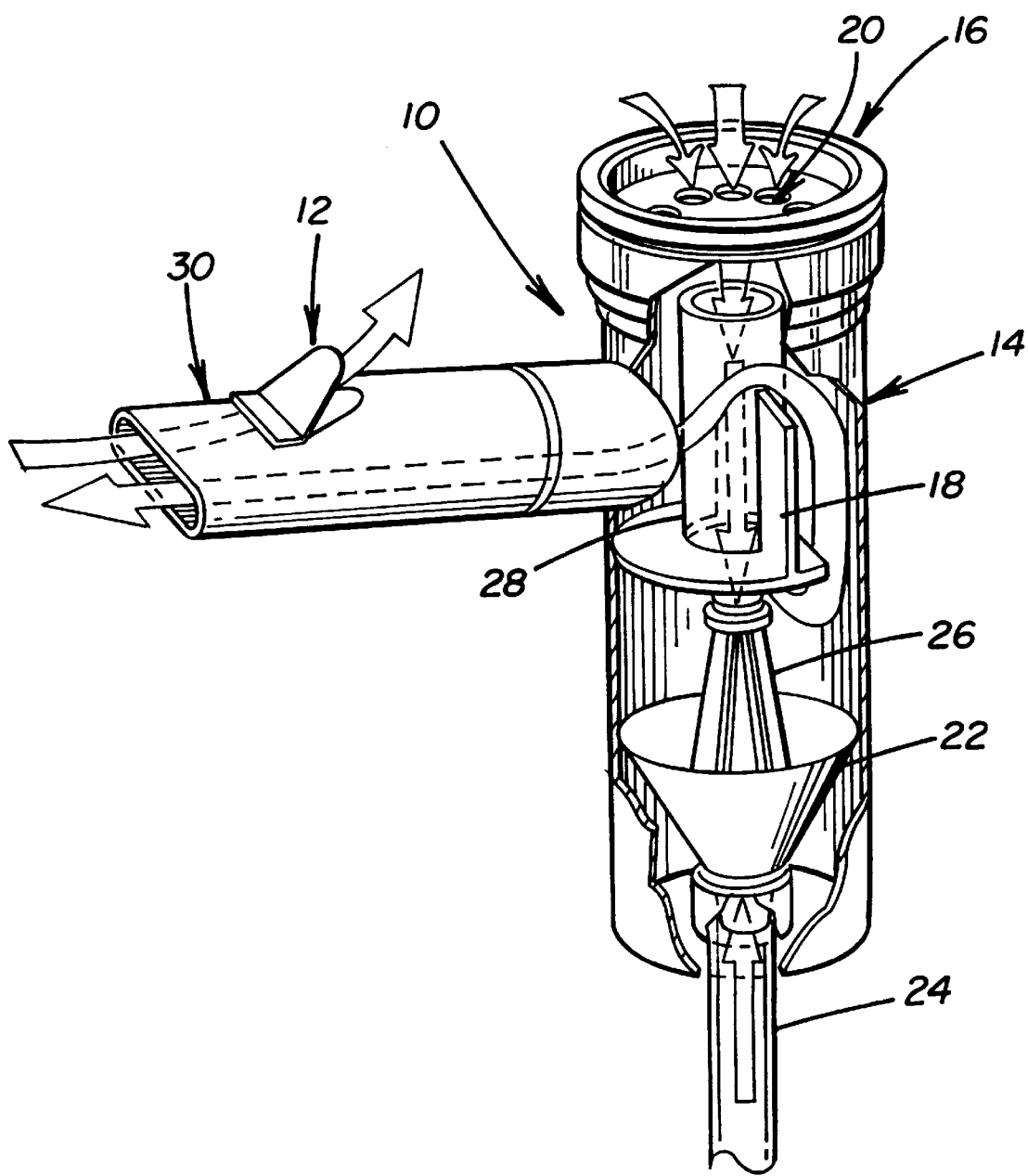
FIG. 3 depicts a jet nebulizer suitable for aerosolization of the concentrated tobramycin solution.

FIG. 3 shows a representative jet nebulizer 10 useful for aerosolization of tobramycin aerosol having particle size predominantly in 1–5μ region. Nebulizer (10) consists of the outside case (14), mouthpiece (30), nebulizer cup (22) covered with cap 16, Venturi chamber (28), air supply tube (24), liquid medicine cup (22) and baffle (18).

The liquid formulation is placed into the nebulizer cup (22) by removing and replacing the cup's cap (16). The cap (16) has one or more air intake holes (20) that allow entrainment of room air to Venturi chamber (28). Venturi chamber (28) allows entrained room air to mix with aerosol to increase drug delivery. Air supply tube (24), typically (8 l/M) is connected to nebulizer's liquid medicine cup (22). Air goes through the cup (22) into jet nebulizer orifice (26) where it creates aerosol by shearing the liquid solution into small threads of liquid that shatter into small particles when it hits a baffle (18). The nebulizer 10 further comprises a mouthpiece (30) for inhalation of aerosol. The mouthpiece contains flapper valve (12) to allow exhalation. The mouthpiece (30) is connected to the main body of the nebulizer (10).

Two main types of nebulizers, jet and ultrasonic nebulizers, were identified as potentially suitable for the purposes of this invention.

Among the available nebulizers, the jet nebulizers known as Sidestream®, obtained from Medicaid and Pari LC® obtained from Pari Respiratory Equipment, Richmond, Va., were found to produce an aerosol with potentially respirable characteristics. Two ultrasonic nebulizers that produce appropriate particle size 1 to 5μ, and have a 5 mL reservoir capacity, are the Aerosonic by DeVilbiss and UltraAire by Omron. These jet and ultrasonic nebulizers, can be advantageously used in the invention.

Recently, the Pari LC jet nebulizer has been modified in that a one-way flow valve was added. The modified nebulizer was renamed the Pari LC Plus™ and is commercially available for PARI Respiratory Equipment, Richmond, Va. In vitro experiments using a test lung show that the Pari LC Plus delivers up to 20% more drug than the Pari LC jet nebulizer. The particle size in both apparatuses is identical. The one-way valves also decrease the potential for accidental spillage and allow for the use of an expiratory filter.

To select the most efficacious nebulizer, several studies were performed.

A randomized, cross-over study compared the ability of several nebulizers to deliver tobramycin by measuring peak sputum tobramycin concentrations in samples collected ten minutes after completion of the aerosol dose. This study used a tobramycin formulation containing about 60 mg/mL tobramycin in 5 mL of ¼ normal saline. In this study, the Pari LC™ jet nebulizer was selected, because of a short time (about ten minutes) in which it is able to complete nebulization of all 5 mL of tobramycin solution and also because it generates an ideal mass median aerodynamic diameter particles of about 3.3 μm. In this setting, the Pari LC™ jet nebulizer delivered about 678.8 μg/g of tobramycin, measured as a mean peak sputum concentration. In this study, only 13% of all treated patients had sputum concentrations lower than 128 μg/g. All other patients (87%) achieved sputum concentrations larger or equal to 128 μg/g.

The second study, described below, was designed to determine in vitro which nebulizers meet criteria that are important for delivery of aerosolized antibiotics. Both ultrasonic and jet nebulizers were studied.

The third study was designed to determine the pharmacodynamics of tobramycin in the sputum which is a measure of the efficacy of the aerosol delivery.

An in vitro comparative study evaluated a variety of commercially available jet nebulizers, including among others, the Acorn II® by Marquest, T-Updraft® by Hudson, Sidestream® by Medicaid, and Pari LC® by Pari. The PulmoAide® compressor was chosen because of its reliability and widespread use.

Studies of these nebulizers revealed that most of them are relatively inefficient in delivering an inhalable mist. The three chosen nebulizers used in the clinical protocols, the ultrasonic DeVilbiss 99, the Pari LC jet and the Medicaid Sidestream jet, have shown properties suggesting that they could possibly deliver tobramycin aerosol into endobronchial space. Of the three, two jet nebulizers were clearly superior to the ultrasonic DeVilbiss nebulizer. Therefore, they have been evaluated to determine which one of them could provide the greatest amount of drug to the airways and two jet nebulizers were found to meet the requirements.

A comparative characteristics of the Ultraneb 99 DeVilbiss (ultrasonic) and two of the jet nebulizers, the Sidestream and the Pari LC with the PulmoAide compressor, showing best characteristics, are listed in Table 3.

TABLE 3

Comparative Characteristics of Different Nebulizers

| Nebulizer | DeVilbiss 99 | Sidestream | Pari LC |
| --- | --- | --- | --- |
| Type | Ultrasonic | Jet | Jet |
| Airflow | 8 L/m | 8 L/m | 8 L/m |
| Liquid Reservoir | 30 mL | 5 mL | 5 mL |
| Time to Nebulize | 10–12 minutes | ~13 minutes(*) | 10 minutes(**) |
| Tobramycin | 20 mg/mL | 60 mg/mL | 60 mg/mL |
| Formulation | in ½ NS | in ¼ NS | in ¼ NS |
| Aerosol Reservoir | 1,200 mL | 30 mL | 30 mL |
| MMAD** | ~4–5 microns | ~2.2 microns | ~4–5 microns |
| Drug Dose/mL | 33 ± 1.8 mg | 30 ± 1.8 mg | 29 ± 5 mg |
| Total Drug Dose | 600 mg | 300 mg | 300 mg |

*Time to sputtering of jet
**Mass median aerodynamic diameter

Table 3 shows substantial differences between the ultrasonic and jet nebulizer systems. The two jet nebulizers require about six times smaller solution volume and do not have or require a large reservoir from which the aerosol can be inhaled.

Of the two jet nebulizers compared in Table 3, the Sidestream may be more efficient in delivery tobramycin to the lower airway because of the smaller (2.2μ) particle size output. Conversely, the Pari LC produces a larger particle size (4.5μ) at a higher output thus reducing the delivery time and patient's discomfort. The improved version of Pari LC Plus jet nebulizer produces particle sizes 3.3μ, which are the most preferred for treatment of tuberculosis. Both jet nebulizers have a Venturi design which increases drug delivery within inspiration. The smaller equipment size decreases the fallout of aerosolized particles that occurs prior to inspiration by the patient. The jet nebulizers Sidestream and Pari LC also have the advantage of being available in both reusable disposable units.

As also seen in Table 3, all three nebulizers delivered about 30 mg/mL of tobramycin to the airways even though the ultrasonic DeVilbiss 99 nebulizer needed twice as much drug, that is 600 mg of tobramycin compared with 300 mg for the two jet nebulizers, for delivery of 33 mg/mL.

The major limitation of the Ultraneb 99 (DeVilbiss) ultrasonic nebulizer used for delivery of tobramycin formulation are its high-cost, waste of the drug and inconvenience. As seen from Table 3, this nebulizer requires 30 mL of the drug solution, and it has large, 1200 mL aerosol reservoir. In order for tobramycin aerosol therapy to be widely available and used by patients with tuberculosis in ambulatory or home setting, a more efficient and easier to use nebulizer is needed.

Although all suitable nebulizers are intended to be within the scope of this invention, a jet or ultrasonic nebulizers, preferably modified jet nebulizer Pari LC Plus, equipped with Pulmo-Aid compressor are most preferred for the method of the invention.

IV. Efficacy

The efficacy of the method of the invention for therapy, prophylaxis and containment of infectivity depends on the delivery of the aerosolized tobramycin formulation and is determined and predicted by the presence and concentration of tobramycin in sputum. If the concentration of tobramycin found in sputum is sufficient to suppress the *Mycobacterium tuberculosis* infection, then the combination of the regimen/formulation/nebulizer is efficient for treatment, prophylaxis or containment of the infection. The most efficient method is when the regimen of administration regimen delivers the amount of aerosolized drug which is therapeutically effective in the great majority (>90%) of patients, where all or almost all of the drug is delivered into the site of infection, and where delivered drug amount is sufficient to suppress the *Mycobacterium tuberculosis* in sputum.

The measure of the efficacy in this instance is the finding sufficient amount of the nebulized drug in the sputum in >90% of the patients in the treated population. Efficient tobramycin delivery is defined as achieving spectrum concentration ≧10 times the median inhibitory concentration (MIC) of 90% pathogens, that is more than about 80 ug/mL in ≧ the sputum of 90% patients tested.

Because of the difficulty with the sputum absorption of tobramycin, for efficacious therapy, prophylaxis and containment, tobramycin is provided in much higher doses than ten times MIC. These dosages vary according to the treatment, age of the patient, severity of the infection and other criteria for determination of the status of the disease. Therefore, the dosages are from 40 to about 800 mg/total, preferably from about 100 to about 400 mg/total, most preferably about 300 mg/total. These dosages are delivered in a solution of about 3 to about 7 mL, preferably about 5 mL of one quarter strength of normal saline. The above concentration of tobramycin have been found to be optimal for the most efficacious treatment. It is within the scope of the art for an attending physician to determine whether a lower or higher dosage of tobramycin is needed. The 300 mg, i.e. 60 mg/mL dose of tobramycin per one administration is most preferred.

UTILITY

The utility of this invention is based on the finding that high tobramycin concentration formulated in a small volume of diluted or full saline formulation can be used by either a jet or hand-held ultrasonic nebulizer for efficacious delivery of tobramycin to the endobronchial space in human patients suffering from tuberculosis. The method of treatment prevention or containment of tuberculosis according to the invention is safe and efficacious.

EXAMPLE 1

Tobramycin Formulation for Treatment and Prophylaxis of Tuberculosis

This example describes preparation of the formulation of the invention.

Hot water for injection was thoroughly flushed (WFI) through 20 L Millipore product vessel. Tobramycin potency (g/L) was assayed and tobramycin was added to product vessel. The amount of tobramycin was weighed accurately into a wide mouth specimen bottle and labeled. 11.25 kg of WFI was dispersed into a clean 20 L Millipore product vessel. With moderate agitation, 33.75 g sodium chloride, USP, was slowly added and mixed until dissolved. WFI was added to the product vessel to 12 Kg and mixed for 5 minutes, under continual mixing, 100 mL 5 N $H_2SO_4$ (sulfuric acid) was carefully added for each liter of WFI in the final formulation. Product vessel was sparged with nitrogen ($N_2$). After approximately 15 minutes of sparging, dissolved oxygen ($O_2$) was measured by continuous monitoring of dissolved oxygen in the tank, using an oxygen probe. The amount of the dissolved $O_2$ was continued to be monitored until five (5) consecutive measurements reached levels of $\leq 3$ ppm of dissolved $O_2$. With continuous sparging of $N_2$ and under moderate mixing, the tobramycin was added and mixed until dissolved. Twenty mL sample of formulation was removed and pH was measured. The formulation was adjusted to a final pH 6.0. An aliquot of product formula was sampled and analyzed for tobramycin concentration, for pH, and for dissolved $O_2$ (in triplicate). When the batch met quality control testing criteria, the formulation was released and used in clinical setting.

EXAMPLE 2

Tobramycin Formulation—Effect of A Normal and Dilute Saline

This example describes testing performed to determine the effect of normal and quarter strength diluted saline on the aerosolization of tobramycin and on the amount of drug delivered over a ten-minute period.

To test output from a hand-held portable ultrasonic nebulizer, an UltraAirs by Omron was used. This ultrasonic nebulizer has a reusable medication cup that is placed over the ultrasonic crystal. The medication cup was weighed, a 5 mL solution of tobramycin (60 mg/mL) was added and cup reweighed. Tobramycin was dissolved in solution of normal saline (0.9% w/v) or ¼ normal (0.225% w/v) saline. After 10 minutes nebulization run, the cups were reweighed. The aerosolized output of tobramycin was determined from the difference between weight before and after the nebulization. Each solute was tested 14 times. The attached Table 4 shows the results.

Results are shown in Table 4.

TABLE 4

Effect of Saline Dilution on Ultrasonic Nebulizer Delivery of Tobramycin
Comparison of 0.9% NS v. 0.22% NS

|  | MEAN | ST. DEV | VAR | COEF/VAR |
| --- | --- | --- | --- | --- |
| Nondiluted 0.9% NS | 3.635714 | 0.583737 | 0.340749 | 0.160556 |
| ¼ - diluted 0.22% NS | 4.070714 | 0.41174 | 0.16953 | 0.101147 |

Statistical analysis of the results show that the ¼ normal solution delivers a higher amount of drug over a ten-minute period (p=0.031).

Higher amount of tobramycin was delivered when tobramycin was formulated in ¼ diluted saline than tobramycin formulated in full strength nondiluted saline.

EXAMPLE 3

Stability of Tobramycin Formulation

This example describes studies performed for determination of tobramycin formulation stability at a high temperature.

An accelerated stability study of tobramycin 60 mg/mL in 0.225% NS in polyethylene vials, packaged in a nitrogen enriched environment, was carried out for 35 days at 40° C. The higher temperature was chosen to accelerate any degradation process. Vials at target pH 5.5, 6.5 and 7.0 were studied at Day 0 and Day 35. Color was examined by Klett-Summerson (KS) U.S. scale. The KS is used to measure color and color changes in liquid pharmaceutical formulations. A KS value of 0 would be colorless solution, 200 would typically be a strong amber color. The human eye can first detect a tint at about a KS scale of 20. Typically a change of KS scale from the 0–20 range (a colorless solution) to a value greater than 200 would be a limiting factor in stability studies even though the drug in the formulation may still be potent.

Since *Drug Develop Industr. Pharm.*, 18:1423–36 (1992) details that the major degradation process for tobramycin is oxygen dependent, the packaging was done in a nitrogen enriched environment. Results are summarized in Table 5.

TABLE 5

Results of 35 Day Stability Study at 40° C.

| Target pH | N | Time (days) | Actual pH (Mean) | Color KS units (Mean) |
| --- | --- | --- | --- | --- |
| 5.5 | 3 | 0 | 5.55 | 13 |
| 5.5 | 5 | 35 | 5.51 | 104 |
| 6.5 | 3 | 0 | 6.57 | 12 |
| 6.5 | 5 | 35 | 6.56 | 107 |
| 7.0 | 3 | 0 | 7.07 | 13 |
| 7.0 | 5 | 35 | 7.04 | 171* |

*p < .05 compared to 5.5 and 6.5.

KS units express color changes as described above.

Polyethylene LDPE vials were used for three pH values. Each vial contains 60 mg/mL tobramycin in 5 mL of 0.225% NS, 5 mL total volume and was stored in foil overpouch nitrogen enriched environment. Color and actual pH testing was done at a time and after a storage for 35 days at 40° C.

The results seen in Table 5 are surprising as a color of the formulation appears to be dependent upon pH of the formulation. The development of the color is an early marker of tobramycin degradation and an undesirable product characteristic. The formulation dependence on the pH shows that the optimal pH for the tobramycin formulation is in the pH 5.5 to 6.5 range.

Furthermore, the rapid coloring of the solution at 40° C. teaches that storage at lower temperatures such as 5° C. to 25° C. including refrigeration, is desirable.

EXAMPLE 4

Extended Stability Study

An extended stability study for tobramycin had the following study design.

Two separate batches of tobramycin were formulated at 60 mg/mL tobramycin in ¼ normal saline at pH 6.0 The solution was packaged in low-density polyethylene vials at 5 mL per vial, stored in foil overpouches that were purged with nitrogen. Stability studies for 3 samples per test point were initiated at 5° C. and 25° C.

The first two batches (I and II) were stored in pouch at 5° C. for 6 months. The second two batches (III and IV) samples were stored in pouch at 25° C. for 6 months. In all these batches, color, tobramycin concentration, tobramycin impurities, pH stability, and oxygen were assayed.

TABLE 6

Extended Stability Study I
Baseline, 3-Month and 6-Month Data at 5° C.

| Assay Description | Units | Limits | Initial | 3 Mo | 6 Mo |
|---|---|---|---|---|---|
| pH | | 5.5–6.5 | 6.0 | 6.1 | 6.2 |
| Tobramycin | mg/mL | 54.0–72.0 | 59.0 | 58.3 | 57.2 |
| Chloride as Sodium Chloride | mg/mL | 2.02–2.48 | 2.24 | 2.30 | 2.24 |
| Color | KS | 0–200 | 15 | 19 | 18 |
| Visual Inspection | | Pass | Pass | Pass | Pass |
| Impurities - Peak D | % | 0.00–5.00 | ND | 0.00 | 0.00 |
| Impurities - Peak X | % | 0.00–5.00 | ND | 0.00 | 0.00 |
| Annular Oxygen Conc. | % | 0.00–5.00 | 4.68 | 4.78 | 4.08 |

ND = None Detected
Product: 60 mg/mL Tobramycin formulated for inhalation
Container: Rexene 6010 LDPE
Container Volume: 5 mL
Fill Volume: 5 mL
Storage Condition: 5° C.
Sterilization: Aseptic Fill
Overpouch: Preformed Laminated Foil

TABLE 7

Extended Stability Study II
Baseline, 3-Month and 6-Month Data at 5° C.

| Assay Description | Units | Limits | Initial | 3 Mo | 6 Mo |
|---|---|---|---|---|---|
| pH | | 5.5–6.5 | 5.8 | 6.1 | 6.0 |
| Tobramycin | mg/mL | 54.0–72.0 | 60.3 | 59.5 | 59.4 |
| Chloride as Sodium Chloride | mg/mL | 2.02–2.48 | 2.29 | 2.30 | 2.31 |
| Color | KS | 0–200 | 22 | 20 | 25 |

TABLE 7-continued

Extended Stability Study II
Baseline, 3-Month and 6-Month Data at 5° C.

| Assay Description | Units | Limits | Initial | 3 Mo | 6 Mo |
|---|---|---|---|---|---|
| Visual Inspection | | Pass | Pass | Pass | Pass |
| Impurities - Peak D | % | 0.00–5.00 | ND | ND | 0.00 |
| Impurities - Peak X | % | 0.00–5.00 | ND | 4.87 | 0.00 |
| Annular Oxygen Conc. | % | 0.00–8.00 | 4.87 | 4.66 | 4.06 |

ND = None Detected
Product: 60 mg/mL Tobramycin formulated for inhalation
Container: Rexene 6010 LDPE
Container Volume: 5 mL
Fill Volume: 5 mL
Storage Condition: 5° C.
Sterilization: Aseptic Fill
Overpouch: Preformed Laminated Foil

TABLE 8

Extended Stability Study III
Baseline, 3-Month and 6-Month Data at 25° C.

| Assay Description | Units | Limits | Initial | 3 Mo | 6 Mo |
|---|---|---|---|---|---|
| pH | | 5.5–6.5 | 6.0 | 6.3 | 6.1 |
| Tobramycin | mg/mL | 54.0–72.0 | 59.0 | 58.5 | 57.4 |
| Chloride as Sodium Chloride | mg/mL | 2.02–2.48 | 2.24 | 2.24 | 2.25 |
| Color | KS | 0–200 | 15 | 34 | 52 |
| Visual Inspection | | Pass | Pass | Pass | Pass |
| Impurities- Peak D | % | 0.00–5.00 | ND | 0.00 | 0.04 |
| Impurities - Peak X | % | 0.00–5.00 | 0.00 | 0.05 | 0.07 |
| Annular Oxygen Conc. | % | 0.00–8.00 | 4.68 | 4.62 | 4.47 |

ND = None Detected
Product: 60 mg/mL Tobramycin formulated for inhalation
Container: Rexene 6010 LDPE
Container Volume: 5 mL
Fill Volume: 5 mL
Storage Condition: Room Temperature (25°)
Sterilization: Aseptic Fill
Overpouch: Preformed Laminated Foil

TABLE 9

Extended Stability Study IV
Baseline, 3-Month and 6-Month Data at 25° C.

| Assay Description | Units | Limits | Initial | 3 Mo | 6 Mo |
|---|---|---|---|---|---|
| pH | | 5.5–6.5 | 5.8 | 6.1 | 5.9 |
| Tobramycin | mg/mL | 54.0–72.0 | 60.3 | 60.1 | 59.4 |
| Chloride as Sodium Chloride | mg/mL | 2.02–2.48 | 2.29 | 2.30 | 2.31 |
| Color | KS | 0–200 | 22 | 52 | 73 |
| Visual Inspection | | Pass | Pass | Pass | Pass |
| Impurities - Peak D | % | 0.00–5.00 | 0.00 | 0.03 | 0.05 |

TABLE 9-continued

Extended Stability Study IV
Baseline, 3-Month and 6-Month Data at 25° C.

| Assay Description | Units | Limits | Initial | 3 Mo | 6 Mo |
|---|---|---|---|---|---|
| Impurities - Peak X | % | 0.00–5.00 | ND | 0.00 | 0.07 |
| Annular Oxygen Conc. | % | 0.00–8.00 | 4.87 | 4.38 | 4.69 |

ND = None Detected
Product: 60 mg/mL Tobramycin formulated for inhalation
Container: Rexene 6010 LDPE
Container Volume: 5 mL
Fill Volume: 5 mL
Storage Condition: Room Temperature (25°)
Sterilization: Aseptic Fill
Overpouch: Preformed Laminated Foil As seen from Tables 5–9, color of the tobramycin solution did not change substantial even during extended storage at 5° or 25° C. confirming the good stability of the tobramycin solution under the stated study conditions.

After six months at 5° C., neither of two batches had shown any changes outside of set limits. At 25° C. storage, the only observed change was the formation of low levels of color, with the two batches showing increases from 15 KS units to 52 KS units and from 22 KS units to 73 KS units.

The formulation at high concentration at the optimum pH of 6 is thus completely stable at 5° C. After six months at 25° C., the formulation is effectively stable, remaining well within an acceptable range of color.

EXAMPLE 5

Testing Nebulizers

This example describes a study performed in order to determine criteria for selection of a suitable nebulizer for delivery of aerosolized tobramycin.

A study was conducted at the University of Washington to determine the tobramycin formulation required to achieve a sputum concentration between 128 μg/gm and 1000 μg/gm sputum at 10 minutes post-completion of aerosol administration from a Sidestream jet nebulizer using a PulmoAide compressor and a Pari LC jet nebulizer using a PulmoAide compressor.

Patients received serial doses of 300 mg tobramycin (5 mL of a 60 mg/mL solution in ¼ NS) from each of the two jet nebulizers. The doses were separated by at least 2 days and not more than 5 days. Peak serum and sputum concentrations were assessed and results are seen in Tables 10 and 11.

TABLE 10

Sputum Concentrations Following Aerosol Administration of 300 mg Tobramycin in 5 mL of ¼ NS

| Subject # | Jet Nebulizer | Baseline | Sputum Tobramycin Concentrations (μg/gm) 10 min.* | 1 hour* | 2 hours* |
|---|---|---|---|---|---|
| 001 | Sidestream | bql† | 792.8 | 1026.7 | 163 |
| | Pari LC | bql | 1595.9 | 481.8 | 416.8 |
| 002 | Sidestream | bql | 460.6 | 23.1 | 49.1 |
| | Pari LC | bql | 764.2 | 231.8 | 52.8 |
| 003 | Sidestream | bqi | 162.5 | 180.5 | 58.1 |
| | Pari LC | bql | 133.7 | 110.7 | 92.5 |
| 004 | Sidestream | bql | 84.2 | 36.6 | 57.5 |
| | Pari LC | bql | 166.5 | 32.4 | 60.5 |
| 005 | Sidestream | bql | 1135.9 | 488.2 | 331.5 |
| | Pari LC | bql | 1395.6 | 186.8 | 131.8 |
| | Mean/Std | bql | 527.21 ± 585.9 | 488.2 | 331.5 |
| | Dev | bql | 395.6 ± 677.2 | 186.8 | 131.8 |

*Timed from completion of aerosol treatment
†<20 μg/gm

TABLE 11

Serum Concentrations Following Aerosol Administration of 300 mg Tobramycin in 5 mL of ¼ NS

| Subject # | Jet Nebulizer | Baseline | Serum Tobramycin μg/mL 1 hour* | 2 hours* | ± % change $FEV_1$* 30 min* |
|---|---|---|---|---|---|
| 001 | Sidestream | not detected | 0.3 | 0.2 | −2.2% |
| | Pari LC | not detected | 0.2 | 0.3 | −1.2% |
| 002 | Sidestream | not detected | 0.2 | 0.2 | 0.0% |
| | Pari LC | not detected | 0.5 | 0.4 | 1.2% |
| 003 | Sidestream | not detected | 0.9 | 0.8 | −7.6% |
| | Pari LC | not detected | 0.6 | 0.5 | −0.6% |
| 004 | Sidestream | not detected | 1.2 | 1.0 | −1% |
| | Pari LC | not detected | 0.5 | 0.4 | −2% |
| 005 | Sidestream | not detected | 1.6 | 1.0 | 0.0% |
| | Pari LC | not detected | 0.8 | 0.7 | −5% |

*Timed from completion of aerosol treatment
<20 μg/gm

The results show that an aerosolized tobramycin dose of 300 mg in 5 mL of 60 mg/mL in ¼ NS achieved the target concentration of >128 μg/gm in sputum. This dosage was also considered extremely safe because serum concentrations were smaller than <1.6 μg/mL and were, therefore, well below the recommended peak therapeutic serum concentrations 8–10 μg/mL.

EXAMPLE 6

Safety and Efficacy of Tobramycin Treatment Selection of Patients

This example describes a study for safety and efficacy of tobramycin formulation for treatment of tuberculosis.

In this study, the efficacy and safety parameters are assessed for tobramycin formulation containing 300 μg of tobramycin administered twice daily for five days to patients with newly diagnosed pulmonary tuberculosis.

The efficacy is determined for each nebulizer by measuring concentration of tobramycin in sputum 10 minutes after completion of nebulization. Concentration of ≧128 μg/gm of sputum is considered adequate.

The safety parameters assessed are:

Incidence of treatment related adverse reactions occurring during the administration of the aerosolized tobramycin by the different nebulizer delivery systems.

Presence or occurrence of acute bronchospasm at the time of drug administration.

Absorption of tobramycin into the systemic circulation.

Pari LC Jet nebulizer with PulmoAide compressor (at 8 L/min) containing a 5 mL solution of 60 mg/mL tobramycin sulfate in ¼ NS.

Twenty patients are enrolled in each study. Each patient receives, in random order, one administration from each nebulizer delivery system. Each aerosol administration is separated by a minimum of 48 hr. Sputum samples are collected at baseline, 10 minutes, 1 hr and 2 hr post-completion of the aerosol drug administration to measure tobramycin concentration. Serum samples are collected at baseline, 1 hr and 2 hr post-completion of aerosol administration to measure tobramycin levels. Airway irritation and acute bronchospasm are assessed by measuring spirometry immediately prior to and 30 min post-completion of aerosol administration. A decrease in forced expiratory volume ($FEV^1$)>15% in the 30 min spirometry test is considered evidence of bronchospasm.

The primary objective of this study is to determine if the jet nebulizers tested can aerosolize sufficient tobramycin sulfate to achieve a peak sputum tobramycin concentration of 128 µg/gm or greater in at least 85% of patients with tuberculosis measured 10 minutes after the completion of nebulization. The dose used with the ultrasonic nebulizer (20 mg/mL in 30 mL ½ NS) is included as a control.

The second objective is to determine whether the tobramycin concentration required to achieve a peak sputum concentration of 128 µg/gm or greater is safe and well tolerated by the patient. Safety is defined as a lack of acute bronchospasm and minimal systemic absorption.

All patients with underlying disease of tuberculosis, confirmed at entry by the inclusion/exclusion criteria specified in this protocol, are eligible for enrollment into the study. Investigators at the participating TBC centers select patients that meet all of the inclusion criteria and one of the exclusion criteria.

Eligible patients are admitted to the study center on the day of the study and receive aerosol therapy if they fulfill entrance criteria.

Physical exam is administered by a physician or RC nurse prior to initial aerosol treatment only.

Vital signs, height, weight, oximetry, assessment of current respiratory status and brief medical history are recorded.

Sputum and serum samples are collected to measure baseline tobramycin concentrations.

Patients sat upright and used nose clips during the aerosol administration. The total duration of time and the number of inhalations required to complete the aerosol treatment are recorded. Any evidence of wheezing or respiratory distress are recorded as well as number of rest periods required by the subject because of dyspnea or excessive coughing during the administration period.

Immediately after completing the aerosol therapy, the subject is asked to rinse with 30 mL of normal saline through the mount, gargle for 5–10 seconds and expectorate the rinse. This is repeated for a total of three rinses. Sputum specimens are collected at 10 minutes after rinsing oral cavity and 2 hours after completion of the aerosol drug administration. Serum is collected at 1 and 2 hours after completion of the aerosol drug administration for determination of the tobramycin levels. Spirometry is obtained 30 minutes following completion of the aerosol drug administration. Following the last aerosol treatment of the study, patients receive a brief physical exam after post-spirometry has been measured.

What is claimed is:

1. A method for treatment and containment of infectivity of pulmonary tuberculosis by providing a patient in need of such treatment an aerosol formulation comprising aerosolized tobramycin, said method comprising a step:
   (a) administering to the patient a nebulized aerosol formulation consisting essentially of from about 40 to about 800 mg tobramycin dissolved in full strength or diluted saline adjusted to pH between 5.5 and 7.0 using a nebulizer producing an aerosolized tobramycin of particles sizes of which a mass medium average diameter is predominantly between 1 and 5µ once or twice daily at least until a count of *Mycobacterium tuberculosis* decreases to less than $10^3$.

2. The method of claim 1 wherein the formulation is consisting essentially of from about 80 to about 300 mg of tobramycin dissolved in about 3 to about 5 mL of the full strength or diluted saline adjusted to pH between about 5.5 and 6.5.

3. The method of claim 2 wherein said formulation is consisting essentially of 300 mg of tobramycin administered by a jet nebulizer able to produce aerosol particle sizes predominantly between about 1 and about 5 microns.

4. The method of claim 1 suitable for therapy of pulmonary tuberculosis wherein the treatment comprises administration of aerosolized tobramycin in concentration from about 100 to about 400 mg twice daily for at least five days or more.

5. The method of claim 4 wherein the treatment comprises administration about 200 to about 300 mg of aerosolized tobramycin per one treatment.

6. The method of claim 5 wherein the treatment comprises administration of aerosolized tobramycin in concentration of about 300 mg.

7. A method for containment of infectivity of pulmonary tuberculosis in a patient infected with *Mycobacterium tuberculosis* by providing said patient a tobramycin aerosol formulation, said method comprising steps:
   (a) administering to said patient a nebulized tobramycin aerosol formulation consisting essentially of from about 40 to about 800 mg tobramycin dissolved in the full strength or diluted saline adjusted to pH between 5.5 and 7.0 using a nebulizer producing an aerosolized tobramycin of particles sizes of which a mass medium average diameter is predominantly between 1 and 5µ, said formulation administered once or twice daily;
   (b) continuing such treatment until inhibition of at least 95% of susceptible *Mycobacterium tuberculosis* in endobronchial space of lower lungs, upper lung, alveoli, larynx and pharynx of said patient is achieved or until a count of *Mycobacterium tuberculosis* decreases to less than $10^3$.

8. The method of claim 7 wherein the tobramycin formulation is consisting essentially of from about 80 to about 300 mg of tobramycin dissolved in about 1 to about 5 mL of normal or diluted saline.

9. The method of claim 7 wherein the tobramycin formulation is consisting essentially of from about 100 to about 200 mg of tobramycin dissolved in about 1 to about 5 mL of normal or diluted saline.

10. The method of claim 7 wherein tobramycin aerosol formulation is consisting essentially of from about 300 to about 600 mg of tobramycin dissolved in about 1 to about 5 mL of normal or diluted saline.

11. The method of claim 4 wherein the treatment further comprises administration of a concentrated tobramycin solution consisting essentially of 100 to 600 mg of tobramycin by spray or smear.

12. An aerosol formulation suitable for treatment of pulmonary infection, said formulation consisting essentially of from about 40 to about 800 mg of tobramycin dissolved in about 3 to about 7 mL of a normal or diluted saline adjusted to pH between about 5.5 and 7.0 and administered by aerosolization using a jet or ultrasonic nebulizer able to produce aerosol particle sizes predominantly between 1 and 5μ.

13. The formulation of claim 12 wherein the saline is a quarter normal saline.

14. The formulation of claim 13 wherein the nebulizer is the jet nebulizer and wherein the pH of the formulation is adjusted to about 5.5 to about 6.0.

15. The formulation of claim 13 wherein the nebulizer is the ultrasonic nebulizer and wherein the pH of the formulation is adjusted to about 5.5 to about 6.0.

16. The formulation of claim 14 consisting essentially of from about 100 to about 400 mg of tobramycin dissolved in about 5 mL of quarter normal saline solution.

17. The formulation of claim 16 consisting essentially of about 300 mg of tobramycin.

18. A method for treatment of *Mycobacterium tuberculosis* infections comprising steps:
   (a) administering to upper lung, lower lung and sputum of a patient infected with *Mycobacterium tuberculosis* twice a day an aerosol formulation consisting essentially of about 300 mg of tobramycin dissolved in about 5 mL of solution containing a quarter normal saline adjusted to pH between about 5.5 and 6.5 by nebulization using a jet or ultrasonic nebulizer able to produce predominantly aerosol particle size between 1 and 5μ;
   (b) periodically determining a count of *Mycobacterium tuberculosis* in the patient's sputum; and
   (c) continuing the treatment of step (a) until the count of *Mycobacterium tuberculosis* in sputum is lower than $10^3$ or until undetectable.

19. A method for prophylactic treatment of an individual exposed to a *Mycobacterium tuberculosis* infection and showing a determinable count of *Mycobacterium tuberculosis* but not experiencing tuberculosis symptoms, said method comprising steps:

(a) determining a presence of *Mycobacterium tuberculosis* in the sputum of individual exposed to the infection;
   (b) administering to the individual exposed to the *Mycobacterium tuberculosis* infection a nebulized tobramycin formulation of consisting essentially of about 200 to about 300 mg of tobramycin, once or twice a day for at least five days,
       wherein said tobramycin is dissolved in about 3 to 5 mL of normal or quarter normal saline adjusted to pH between about 5.5 and 6.5; and
       wherein said formulation is administered by a jet or ultrasonic nebulizer producing an aerosol having a particle sizes predominantly between about 1 and about 5 microns,
       said aerosol delivering a sufficient amount of tobramycin to upper airways, lower airways and sputum to eradicate the *Mycobacterium tuberculosis*; and
   (c) determining an absence of *Mycobacterium tuberculosis* in sputum following the treatment.

20. A method for prophylactic treatment of an individual exposed to a *Mycobacterium tuberculosis* infection but not showing a detectable count of *Mycobacterium tuberculosis*, said method comprising steps:

(a) administering to the individual exposed to the *Mycobacterium tuberculosis* infection a nebulized tobramycin formulation consisting essentially of about 100 to about 200 mg of tobramycin, once or twice a day for at least five days,
       wherein said tobramycin is dissolved in about 3 to 5 mL of normal or quarter normal saline adjusted to pH between about 5.5 and 6.5; and
       wherein said formulation is administered by a jet or ultrasonic nebulizer producing an aerosol having a particle sizes predominantly between about 1 and about 5 microns,
       said aerosol delivering a sufficient amount of tobramycin to upper airways, lower airways and sputum to eradicate the *Mycobacterium tuberculosis*; and
   (b) confirming an absence of *Mycobacterium tuberculosis* in sputum following the treatment.

* * * * *